United States Patent [19]

Shinnar et al.

[11] Patent Number: 5,734,015
[45] Date of Patent: Mar. 31, 1998

[54] FAMILY OF LINEAR ANTIMICROBIAL PEPTIDES FROM HAGFISH INTESTINE

[75] Inventors: Ann Shinnar, Teaneck, N.J.; Michael A. Zasloff, Merion, Pa.; Thomas Uzzell, Champagne, Ill.

[73] Assignee: Magainin Pharmaceuticals Inc., Plymouth Meeting, Pa.

[21] Appl. No.: 665,543

[22] Filed: Jun. 18, 1996

Related U.S. Application Data

[60] Provisional application No. 60/000,325 Jun. 15, 1995.
[51] Int. Cl.$^6$ .......................................................... C07K 7/00
[52] U.S. Cl. ..................................................... 530/324; 514/12
[58] Field of Search ............................... 530/324; 514/12

[56] References Cited

U.S. PATENT DOCUMENTS 5,254,537 10/1993 Zasloff ........................................ 514/13

OTHER PUBLICATIONS

Peter J. Hanley, et al., *Proc. Natl. Acad. Sci. USA, Immunology*, "Hagfish Humoral Defense Protein Exhibits Structural and Functional Homology with Mammalian Complement Components," vol. 89, pp. 7910–7914, Sep. 1992.

Judith Varner, et al., *Proc. Natl. Acad. Sci. USA, Immunology*, "A Serum Heterodimer from Hagfish (*Eptatretus Stoutii*) Exhibits Structural Similarity and Partial Sequence Identity with Immunoglobulin," vol. 88, pp. 1746–1750, Mar. 1991.

Allen et al., "Synthesis of 5–and 7–Bromotryptophan and of [5–Bromotryptophan$^9$]–β–corticotrophin–(1_24)–tetracosapeptide, a Highly Potent Corticortrophin Analogue," *J. Chem. Soc., Perkin Transactions I*, pp. 1928–1932 (1980).

Reid et al., "Immunohistochemical Localisation of Bioactive Peptides and Amines Associated with the Chromaffin Tissue of Five Species of Fish," *Cell & Tissue Res.*, 230:499–512 (1995); (*Biological Abstracts*, vol. 5, Abst. No. 63640 (1995)).

Shinnar et al., "New Family of Linear Antimicrobial Peptides from Hagfish Intestine Contains Bromo–tryptophan as Novel Amino Acid," *Peptides Chemistry, Structure and Biology*, Kaumaya et al., eds., Mayflower Scientific Ltd., pp. 189–191 (1996).

Shinnar et al., "New Family of Linear Antimicrobial Peptides from Hagfish Intestine Contains Bromo–tryptophan as Novel Amino Acid," Abstract Form—Fourteenth American Peptide Symposium, Columbus, Ohio Jun. 18–23, 1995.

Shinnar et al., "New Family of Linear Antimicrobial Peptides from Hagfish Intestine Contains Bromo–tryptophan as Novel Amino Acid," Program of Sessions for the Fourteenth American Peptide Symposium, Columbus, Ohio Jun. 18–23, 1995.

*Primary Examiner*—Cecilia J. Tsang
*Assistant Examiner*—C. Delacroix-Muirheid
*Attorney, Agent, or Firm*—Finnegan, Henderson, Farabow, Garrett & Dunner, L.L.P.

[57] ABSTRACT

A new family of linear antimicrobial peptide from hagfish intestine is described. This invention relates to proteins with antimicrobial properties isolated from hagfish intestine and their corresponding chemical sequences. The antibiotics obtained include, but are not limited to, peptides having a sequence selected from the group consisting of:

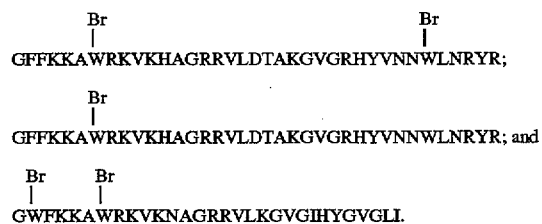

2 Claims, 1 Drawing Sheet

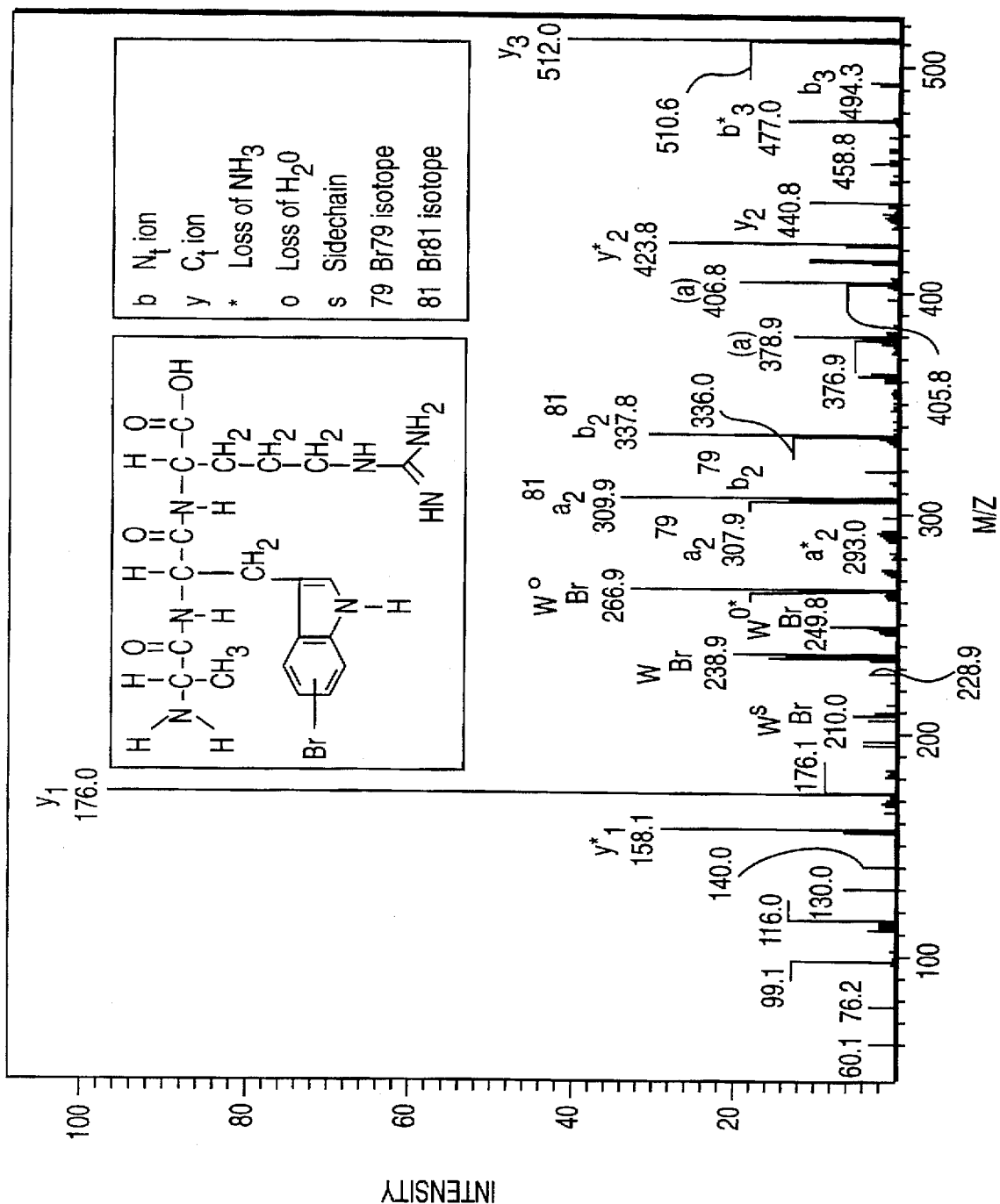

FAMILY OF LINEAR ANTIMICROBIAL PEPTIDES FROM HAGFISH INTESTINE

CROSS REFERENCE TO RELATED APPLICATION

This application claims the benefit of U.S. Provisional Application Ser. No. 60/000,325 filed on Jun. 19, 1995.

BACKGROUND OF THE INVENTION

In recent years, the quest for new antibiotics has led to the discovery of a variety of naturally occurring substances, including peptides like the insect cecropins, mammalian defensins, frog magainins, and aminosterols like squalamine from dogfish shark. Only a small fraction of the vast diversity of existing species has been explored, but the need for antibiotics with limited toxicity and ready availability continues. Thus, there remains a need for antibiotics from other sources.

SUMMARY OF THE INVENTION

This invention provides an unknown family of peptides with antimicrobial activity, isolated from a primitive vertebrate, the hagfish. The invention includes proteins isolated from hagfish intestine with antimicrobial properties as well as the chemical sequences of the peptides.

It is to be understood that both the foregoing general description and the following detailed description are exemplary and explanatory only and are not restrictive of the invention, as claimed.

The accompanying drawing, which is incorporated in and constitutes a part of this specification, illustrates one embodiment of the invention and together with the description, serves to explain the principles of the invention.

BRIEF DESCRIPTION OF THE DRAWINGS

FIG. 1 provides a graph showing the mass spectrum of the tripeptide of Ala-Trp(Br)-Arg upon trypsinization of HFIAP-1.

DETAILED DESCRIPTION

To provide the unknown family of peptides of the claimed invention, the present inventors investigated the Atlantic hagfish, *Myxine glutinosa*. The hagfish, a jawless vertebrate, is the most primitive vertebrate in existence today and lacks circulating lymphocytes and classical immunoglobulins. Moreover, it feeds by scavenging, thus exposing itself to a whole host of pathogens. Nonetheless, hagfish effectively defend against many pathogens.

As described below, the present inventors have discovered the existence of an unknown family of antibiotic peptides that apparently serve to protect the hagfish. As used herein, antibiotic peptides refer to a sequence of amino acids that demonstrate the ability to kill or disable microorganisms such as bacteria (gram-positive and gram-negative), fungi, and protozoa. An effective amount of such antibiotics provides an amount sufficient to produce a detectable and beneficial reduction in the number of microorganisms.

EXAMPLE 1

To screen hagfish organ systems for the presence of antibiotic peptides, the inventors sacrificed 100 Atlantic hagfish, *Myxine glutinosa*, obtained from Huntsman Marine Science Center and dissected the organs on ice. The organs, specifically, liver and gall bladder, stomach, intestine, skin and eggs, were frozen immediately in liquid nitrogen and then stored in plastic bags in a freezer maintained at $-70°$ C. until further analysis.

EXAMPLE 2

To extract peptides, we used the organic solvents $CH_3CN$/1% TFA and the Folch extraction methodology. We then purified the extracts to homogeneity using a scheme involving size exclusion chromatography with Biogel P30, strong cation exchange chromatography with Polysulfoethylaspartamide, and RPHPLC with C4, C8, and C18 stationary phases. Applying the purified extracts to bacterial lawns of *E. coli* and *Staphylococcus aureas* demonstrated that the intestinal tissue was rich in antimicrobial activity.

EXAMPLE 3

The purified extracts were sequenced by conventional AAA and Edman sequencing methods (Table 1). Chemical sequencing revealed three closely related cationic/amphipathic peptides, each with 2 residues that could not be identified initially by these sequencing methods. After 37 cycles of automated Edman sequencing, peptides 1 and 2 (SEQ ID NOS: 1 and 2 respectively) yielded identical primary structures, although the PTH-residues at positions 7 and 32 were not known. The parent masses, determined by electrospray ionization mass spectrometry (ESI-MS), are consistent with the primary structure determined by Edman sequencing, where positions 7 and 32 are tryptophan and either one or both are substituted with bromine. Peptide 3 (SEQ ID NO: 3) shows 73% homology with peptides 1 and 2 (SEQ ID NOS: 1 and 2, respectively). The most abundant peptide (Table 1, peptide 1 (SEQ ID NO: 1)) was proteolyzed with AspN endopeptidase and then reduced and alkyated. The chemical sequence of these fragments did not contain cysteine, but did reveal UV absorption bands similar to tryptophan, although red-shifted.

TABLE 1

Chemical Sequences of Hagfish Intestinal Antimicrobial Peptides

| Peptide | Sequence | Mass |
|---|---|---|
| 1 | GFFKKAW(Br)RKVKHAGRRVLDTAKGVGRHYVNNW(Br)LNRYR (SEQ ID NO:1) | 4643.3 |
| 2 | GFFKKAW(Br)RKVKHAGRRVLDTAKGVGRHYVNNWLNRYR (SEQ ID NO:2) | 4564.0 |
| 3 | GW(Br)FKKAW(Br)RKVKNAGRRVLKGVGIHYGVGLI (SEQ ID NO:3) | 3551.9 |

EXAMPLE 4

To determine the identity of the unknown residues, peptide 1 (SEQ ID NO: 1) was trypsinized, the fragments separated, and the unknown fragment was identified by UV chromophore and mass. A tripeptide containing the unknown residue flanked by alanine and arginine was isolated and subjected to tandem electrospray ionization mass spectrometry. The unknown residue was identified as bromo-tryptophane, based both on the peptide's fragmentation pattern and the isotopic distribution (FIG. 1). Ala-Trp (5-Br)-Arg prepared by chemical synthesis exhibited the same fragmentation profile by MS—MS and similar UV spectrum.

EXAMPLE 5

To complete and confirm the peptide sequences, the present inventors created a cDNA library made from hagfish intestinal mRNA that was probed with an oligonucleotide probe based on the homology between peptides 1 and 2 (SEQ ID NOS: 1 and 2, respectively). DNA sequencing indicated triplet codons for tryptophan at the positions for which the Edman sequencing was initially ambiguous. The presence of a glycine codon following the mature sequence suggested that the native peptide might be amidated at the carboxy terminus.

EXAMPLE 6

Chemical synthesis of the sequence (SEQ ID NO. 4) corresponding to Peptides 1 and 2 (SEQ ID NOS: 1 and 2 respectively) containing native (unmodified) tryptophan was achieved by SPPS, using Fmoc chemistry. Antibiotic activity was measured against *E. coli*, *S. aureus*, *P. aeruginosa*, and *C. albicans* and, using standard methodology, yielded minimum inhibitory concentrations (MICs) of 8, 8, 8, and >256 µg/ml, respectively.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An antibiotic having a sequence selected from the group consisting of:

```
         Br
         |
GFFKKAWRKVKHAGRRVLDTAKGVGRHYVNNWLNRYR
                    (SEQ ID NO:1);
   Br
   |
GFFKKAWRKVKHAGRRVLDTAKGVGRHYVNNWLNRYR
                    (SEQ ID NO:2); and
```

```
  Br          Br
  |           |
GWFKKAWRKVKNAGRRVLKGVGIHYGVGLI (SEQ ID NO:3).
```

2. An antibiotic having a sequence:

GFFKKAWRKVKHAGRRVLDTAKGVGRHYVNNWLNRYR
                    (SEQ. ID No. 4).

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 7
        ( D ) OTHER INFORMATION: Note= "Xaa is Brominated Tryptophan"

( i x ) FEATURE:
        ( A ) NAME/KEY: Region
        ( B ) LOCATION: 32
        ( C ) OTHER INFORMATION: Note= "Xaa is Brominated Tryptophan"

( x i ) SEQUENCE DESCRIPTION: SEQ ID NO:1:

```
Gly  Phe  Phe  Lys  Lys  Ala  Xaa  Arg  Lys  Val  Lys  His  Ala  Gly  Arg  Arg
  1              5                          10                         15

Val  Leu  Asp  Thr  Ala  Lys  Gly  Val  Gly  Arg  His  Tyr  Val  Asn  Asn  Xaa
              20                          25                         30

Leu  Asn  Arg  Tyr  Arg
              35
```

( 2 ) INFORMATION FOR SEQ ID NO:2:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region -continued (B) LOCATION: 7
            (C) OTHER INFORMATION: Note= "Xaa is Brominated Tryptophan"

(xi) SEQUENCE DESCRIPTION: SEQ ID NO:2:

Gly Phe Phe Lys Lys Ala Xaa Arg Lys Val Lys His Ala Gly Arg Arg
    1               5                   10                  15

Val Leu Asp Thr Ala Lys Gly Val Gly Arg His Tyr Val Asn Asn Trp
                    20                  25                  30

Leu Asn Arg Tyr Arg
                35

(2) INFORMATION FOR SEQ ID NO:3:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Region
            (B) LOCATION: 2
            (C) OTHER INFORMATION: Note= "Xaa is Brominated Tryptophan"

(ix) FEATURE:
            (A) NAME/KEY: Region
            (B) LOCATION: 7
            (C) OTHER INFORMATION: Note= "Xaa is Brominated Tryptophan"

(xi) SEQUENCE DESCRIPTION: SEQ ID NO:3:

Gly Xaa Phe Lys Lys Ala Xaa Arg Lys Val Lys Asn Ala Gly Arg Arg
    1               5                   10                  15

Val Leu Lys Gly Val Gly Ile His Tyr Gly Val Gly Leu Ile
                    20                  25                  30

(2) INFORMATION FOR SEQ ID NO:4:

(i) SEQUENCE CHARACTERISTICS:
            (A) LENGTH: 37 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Gly Phe Phe Lys Lys Ala Trp Arg Lys Val Lys His Ala Gly Arg Arg
    1               5                   10                  15

Val Leu Asp Thr Ala Lys Gly Val Gly Arg His Tyr Val Asn Asn Trp
                    20                  25                  30

Leu Asn Arg Tyr Arg
                35